(12) United States Patent
Sauvage et al.

(10) Patent No.: US 10,188,430 B2
(45) Date of Patent: Jan. 29, 2019

(54) DOUBLE-THREADED BONE SCREW

(71) Applicant: CLARIANCE, Beaurains (FR)

(72) Inventors: Bruno Sauvage, Frevin Capelle (FR); Brice Krier, Dainville (FR); Guy Viart, Saint Leger (FR); Nicolas Virgaux, Paris (FR); Pascal Rokegem, Arras (FR); Andrew Clavenna, Dallas, TX (US)

(73) Assignee: CLARIANCE, Beaurains (FR)

( * ) Notice: Subject to any disclaimer, the term of this patent is extended or adjusted under 35 U.S.C. 154(b) by 56 days.

(21) Appl. No.: 15/350,588

(22) Filed: Nov. 14, 2016

(65) Prior Publication Data
US 2017/0135730 A1 May 18, 2017

Related U.S. Application Data

(60) Provisional application No. 62/255,616, filed on Nov. 16, 2015.

(51) Int. Cl.
*A61B 17/70* (2006.01)
*A61B 17/86* (2006.01)

(52) U.S. Cl.
CPC ........ *A61B 17/7032* (2013.01); *A61B 17/863* (2013.01); *A61B 17/7035* (2013.01)

(58) Field of Classification Search
CPC . A61B 17/7032; A61B 17/7034; A61B 17/86; A61B 17/8605; A61B 17/861; A61B 17/8625; A61B 17/863
USPC ......................................... 606/315–317, 323
See application file for complete search history.

(56) References Cited

U.S. PATENT DOCUMENTS

| 3,207,023 | A | * | 9/1965 | Knohl | F16B 25/0031 411/387.3 |
| 3,703,843 | A | * | 11/1972 | Laverty | F16B 25/0031 411/413 |
| 3,861,269 | A |   | 1/1975 | Laverty | |
| 4,329,099 | A | * | 5/1982 | Shimizu | F16B 25/0031 411/412 |
| 5,259,398 | A | * | 11/1993 | Vrespa | A61B 17/863 128/898 |

(Continued)

FOREIGN PATENT DOCUMENTS

EP     1 991 145 B1    11/2008

*Primary Examiner* — Eric S Gibson
(74) *Attorney, Agent, or Firm* — Young & Thompson

(57) ABSTRACT

A discontinuously double-threaded bone screw includes a drive head and anchoring body consisting of a cylindro-conical core over which extend at least two cylindro-conical threads, the anchoring body including anchoring portions of different profiles, ensuring an anchoring corresponding to different bone hardnesses and strengths, the anchoring body including, below the drive head, a first anchoring portion with a conical core and two threads with cylindrical profile and identical pitch, a second anchoring portion with a cylindrical core and a single cylindrical thread over ¼ turn, a third anchoring portion with a cylindrical core and two threads with cylindrical profile over ½ turn, a fourth anchoring portion including a cylindrical core and a single thread with cylindrical profile n turn based on total length of the bone screw, and a fifth anchoring portion including a conical core and two threads with conical profile forming the tip of the bone screw.

7 Claims, 3 Drawing Sheets

(56) References Cited

U.S. PATENT DOCUMENTS

| | | | | |
|---|---|---|---|---|
| 6,030,162 A * | 2/2000 | Huebner | A61B 17/1682 | 411/263 |
| 6,355,043 B1 * | 3/2002 | Adam | A61B 17/72 | 470/27 |
| 7,850,717 B2 * | 12/2010 | Dewey | A61B 17/7001 | 606/246 |
| 8,075,604 B2 * | 12/2011 | Denis | A61B 17/7032 | 606/315 |
| 8,128,671 B2 * | 3/2012 | Taylor | A61B 17/863 | 411/308 |
| 8,382,811 B2 * | 2/2013 | Crook | A61B 17/7037 | 411/412 |
| 8,430,619 B2 * | 4/2013 | Olsen | F16B 25/00 | 411/412 |
| 8,491,302 B2 * | 7/2013 | Arni | A61C 8/0022 | 433/172 |
| 9,055,986 B1 * | 6/2015 | Whipple | A61B 17/863 | |
| 9,155,580 B2 * | 10/2015 | Cormier | A61B 17/7037 | |
| 9,234,539 B2 * | 1/2016 | Gonciarz | F16B 25/0063 | |
| 9,644,668 B2 * | 5/2017 | Taylor | F16B 39/30 | |
| 2004/0141827 A1 * | 7/2004 | Dicke | F16B 5/0275 | 411/413 |
| 2005/0038438 A1 * | 2/2005 | Anderson | A61B 17/7071 | 606/304 |
| 2007/0233122 A1 * | 10/2007 | Denis | A61B 17/7032 | 606/247 |
| 2008/0249579 A1 * | 10/2008 | Taylor | A61B 17/863 | 606/317 |
| 2010/0094352 A1 * | 4/2010 | Iott | A61B 17/8605 | 606/301 |
| 2010/0137918 A1 * | 6/2010 | Wilcox | A61B 17/7037 | 606/301 |
| 2010/0274295 A1 * | 10/2010 | Carls | A61B 17/7041 | 606/305 |
| 2011/0257690 A1 * | 10/2011 | Rezach | A61B 17/7037 | 606/302 |
| 2011/0276095 A1 * | 11/2011 | Bar | A61B 17/863 | 606/279 |
| 2011/0288599 A1 * | 11/2011 | Michielli | A61B 17/7037 | 606/305 |
| 2012/0029579 A1 * | 2/2012 | Bottlang | A61B 17/8042 | 606/315 |
| 2012/0178048 A1 * | 7/2012 | Cottrell | A61C 8/0025 | 433/174 |
| 2013/0218213 A1 * | 8/2013 | Lemoine | A61B 17/7032 | 606/305 |
| 2013/0253595 A1 * | 9/2013 | Zucherman | A61B 17/8625 | 606/305 |
| 2013/0325010 A1 * | 12/2013 | Prien | A61B 17/7216 | 606/64 |
| 2014/0094860 A1 * | 4/2014 | Reimels | A61B 17/844 | 606/323 |
| 2014/0142636 A1 * | 5/2014 | Hes | A61B 17/863 | 606/279 |
| 2014/0236235 A1 * | 8/2014 | Jackson | A61B 17/7037 | 606/267 |
| 2015/0201984 A1 * | 7/2015 | Orbay | A61B 17/863 | 606/304 |
| 2015/0289916 A1 * | 10/2015 | Sharps | A61B 17/863 | 606/315 |
| 2015/0366599 A1 * | 12/2015 | Meng | A61C 8/0018 | 606/315 |
| 2017/0135730 A1 * | 5/2017 | Sauvage | A61B 17/7032 | |

\* cited by examiner

DOUBLE-THREADED BONE SCREW

FIELD OF THE INVENTION

The present invention relates to a double-threaded bone screw which is intended to be screwed into the bone to ensure, for example, the attachment of prostheses or of an implant.

BACKGROUND OF THE INVENTION

From the teaching described in the patents U.S. Pat. Nos. 3,703,843 and 3,861,269, a fastening screw is known for attaching together parts consisting of different materials with different strengths.

The fastening screw comprises a drive head from which extends a cylindrical body provided with two cylindrical threads of identical pitch. Over 1/3 of its length, the cylindrical body comprises two cylindrical threads arranged either at its pointed free end (U.S. Pat. No. 3,703,843) or immediately below the drive head (U.S. Pat. No. 3,861,269).

From the teaching described in the patent EP 1991145, a bone screw is also known which includes a threaded body with cylindro-conical profile, provided at one of its ends with a drive head or with a connector for attaching a linking rod of an osteosynthesis device.

The cylindro-conical body comprises, below its drive head or below the connector, a first threaded section including two helical threads of identical pitch extended by a second threaded section consisting of a single helical thread originating from the first threaded section.

In the case of a bone screw, one notes that the bone tissue into which said screw is implanted exhibits different strengths between its central portion consisting of spongy bone and its peripheral portion consisting of cortical bone.

Indeed, the bone tissue consists of a hard and dense component, the cortical bone, covering a trabecular component, and the less dense and less hard spongy bone. These two components form a continuum with a density gradient that increases as it comes closer to the cortical bone.

SUMMARY OF THE INVENTION

For this purpose, the discontinuously double-threaded bone screw according to the present invention aims to improve bone hold and includes along its anchoring body discontinuous threaded portions ensuring over the entire length of said anchoring body the attachment of said screw in the different components of the bone tissue.

The good mechanical hold of the bone screw according to the present invention in the bone tissue is ensured, on the one hand, by the engagement of the thread in the cortical bone and in the spongy bone, and, on the other hand, by an encapsulation of cortical bone and of spongy bone around the screw and more particularly between the thread turns in order to perfectly fit the profile of said screw.

The discontinuously double-threaded bone screw for the attachment of a prosthesis or of an implant against a bone portion according to the present invention comprises a drive head extended by an anchoring body consisting of a cylindro-conical core over which extend at least two cylindro-conical threads ensuring the bone anchoring of said screw, the anchoring body including, over its entire length and starting from the drive head, anchoring portions of different profile ensuring an anchoring corresponding to the different hardnesses and strengths of the bone, said anchoring body including below the drive head a first anchoring portion consisting of a conical core and two threads with cylindrical profile of identical pitch, a second anchoring portion consisting of a cylindrical core and of a single cylindrical thread over 1/4 turn, a third anchoring portion provided with a cylindrical core and with two threads with cylindrical profile over 1/2 turn, a fourth anchoring portion including a cylindrical core and a single thread with cylindrical profile over n turns as a function of the total length of the bone screw, and a fifth anchoring portion comprising a conical core and two threads with cylindrical profile forming the tip of the bone screw.

The discontinuously double-threaded bone screw according to the present invention comprises a first anchoring portion including two threads with cylindrical profile of identical pitch offset on the periphery of the conical core by 180° degrees.

The discontinuously double-threaded bone screw according to the present invention comprises a fourth anchoring portion including a cylindrical thread that is different from the cylindrical thread provided for the second portion.

The discontinuously double-threaded bone screw according to the present invention comprises an internal bore.

The discontinuously double-threaded bone screw according to the present invention comprises a drive head which consists of a head with spherical profile having in its internal portion a recess for the placement of a tool.

The discontinuously double-threaded bone screw according to the present invention comprises a drive head that consists of a single-piece head with a U-shaped profile intended to receive a tightening screw for the immobilization.

The discontinuously double-threaded bone screw according to the present invention comprises a fifth anchoring portion with a conical profile including self-tapping threads.

BRIEF DESCRIPTION OF THE DRAWINGS

The following description in reference to the appended drawings, which are given as non-limiting examples, will make it possible to better understand the invention, the features that it has, and the advantages that it is capable of procuring.

DETAILED DESCRIPTION OF THE INVENTION

Figure 1:
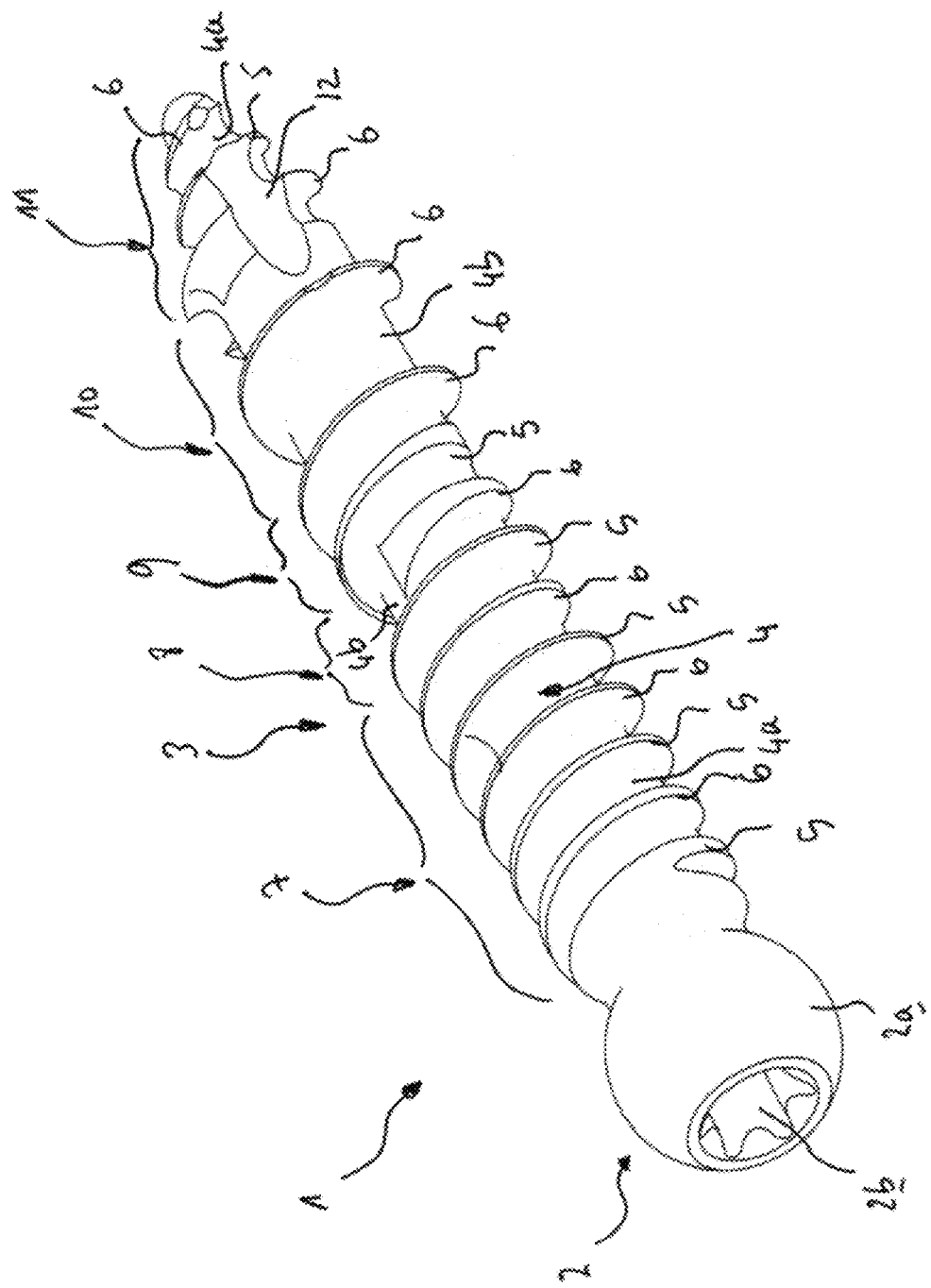
FIG. 1 is a perspective view illustrating the discontinuously double-threaded bone screw according to the present invention.
Figure 2:
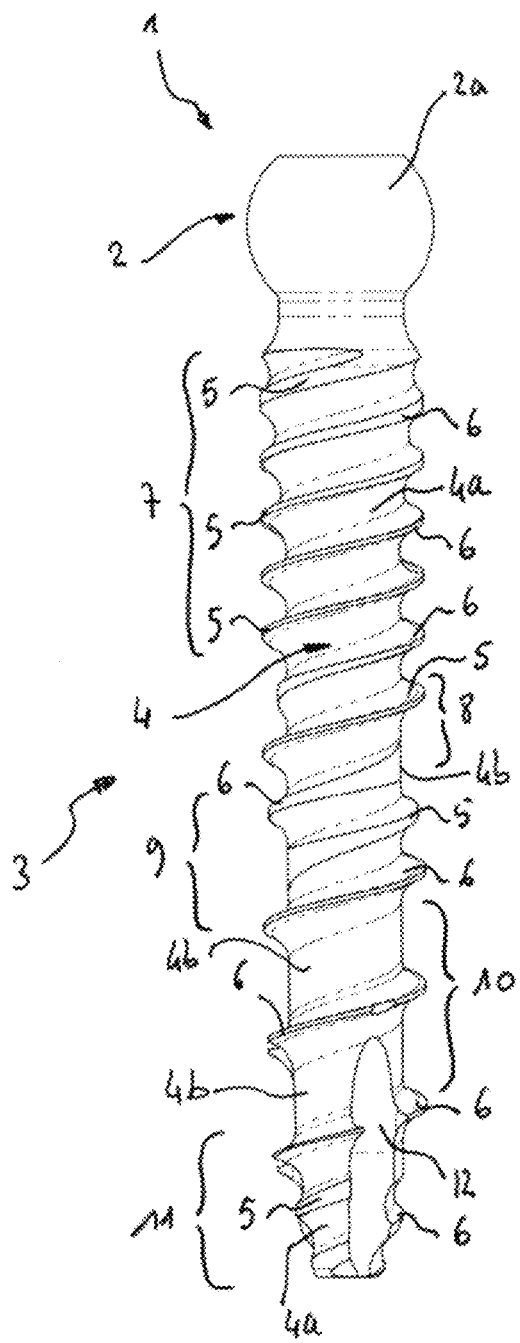
FIGS. 2 and 3 are front and cross-sectional views representing the discontinuously double-threaded bone screw according to the present invention.
Figure 3:
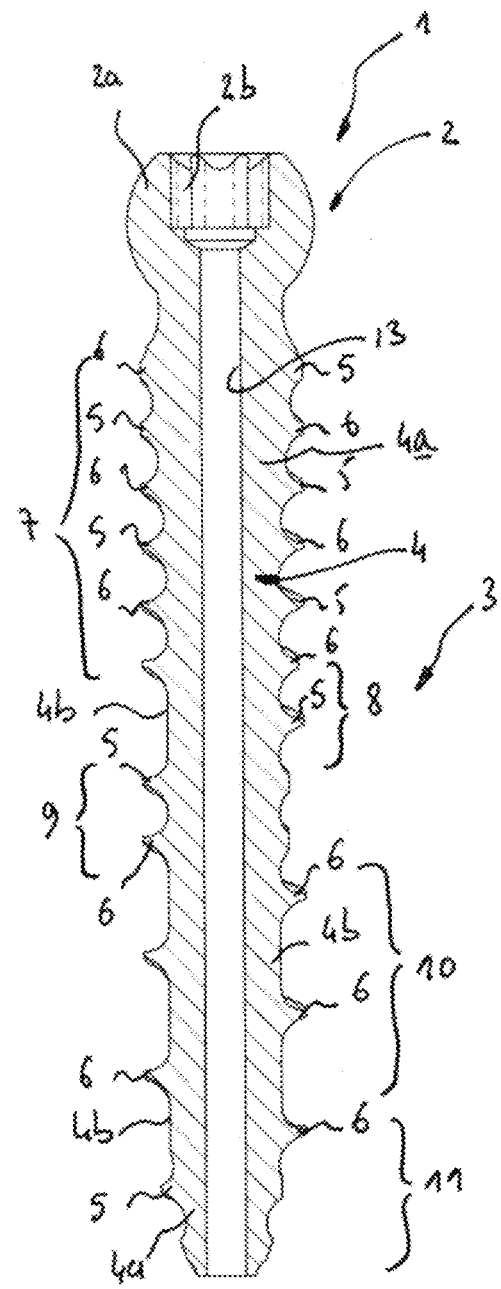

In FIGS. 1 to 3, a bone screw 1 with discontinuous double thread 5, 6, ensuring, for example, the attachment of a prosthesis or of an implant against a bone portion, is shown.

The bone screw 1 comprises a drive head 2 extended by an anchoring body 3 consisting of a cylindro-conical core 4, over which extend at least two discontinuous cylindro-conical threads 5, 6 ensuring the anchoring of said screw 1 in the different components of the bone tissue.

In this first illustration, the drive head 2 can consist of a head with a spherical profile 2a having in its internal portion a recess 2b for the placement of a tool for turning the bone screw 1.

The anchoring body 3 includes, over its entire length and starting from the drive head 2, anchoring portions 7, 8, 9, 10 respectively having different profiles so as to ensure an anchoring corresponding to the different hardnesses and strengths of the bone tissue.

To this effect, the anchoring body 3 comprises, below the drive head 2, a first anchoring portion 7 which consists of the core 4 whose profile is conical 4a here, and of two threads 5, 6 with cylindrical profile and of identical pitch.

The two threads 5, 6 with cylindrical profile are offset on the periphery of the conical core 4a by 180° degrees. In this first anchoring portion 7, the bone screw 1 has a double-threaded anchoring body 3 in order to ensure an engagement and holding of the latter in the cortical bone of the bone tissue.

The anchoring body 3 includes, in the extension of the first anchoring portion 7, a second anchoring portion 8 consisting of the core 4 whose profile is cylindrical 4b in this area and of a single cylindrical thread 5 positioned over ¼ turn of said body.

In this second anchoring portion 8, the second cylindrical thread 6 is stopped so as to allow only the first cylindrical thread 5 to come in contact with the bone tissue during the placement of the screw 1.

The anchoring body 3 comprises, in the extension of the second anchoring portion 8, a third anchoring portion 9 provided with the core 4 whose cylindrical profile 4b is lengthened, and two threads 5, 6 with cylindrical profile arranged over ½ turn of said body.

In this third anchoring portion 9, the second cylindrical thread 6 resumes after stopping in the preceding anchoring portion, while the first cylindrical thread 5 is maintained continuously from the first anchoring portion 7.

Thus, at this third anchoring portion 9, the bone screw 1 has a double-threaded anchoring body 3 over ½ turn in order to augment its impression in the bone tissue.

The anchoring body 3 includes, in the extension of the third anchoring portion 9, a fourth anchoring portion 10 consisting of the core 4 whose profile is cylindrical 4b starting from the second anchoring portion 8, and a single thread 6 with cylindrical profile which extends over n turn as a function of the total length of the bone screw 1.

In this fourth anchoring portion 10, the first cylindrical thread 5 is stopped so as to allow only the second cylindrical thread 6 to come in contact with the bone tissue during the placement of the screw 1. One notes that the fourth anchoring portion 10 includes a cylindrical thread 6 that is different from the cylindrical thread 5 provided for the second portion 8.

The anchoring body 3 comprises, in the extension of the fourth anchoring portion 10, a fifth and last anchoring portion 11 consisting of the core 4 whose profile is again conical 4a and two threads 5, 6 whose profile is also conical, in order to form with the profile of the core 4 the tip of the bone screw 1.

In this fifth anchoring portion 11, the bone screw 1 has a double-threaded anchoring body 3 ensuring the penetration of the latter in the cortical bone of the bone tissue.

Moreover, the fifth anchoring portion 11 of the bone screw 1, and more particularly its tip, comprises recesses 12 that vertically intersect the profile of the two threads 5 and 6.

Each recess 12 positioned on the periphery of the tip of the bone screw 1 constitutes, on the threads 5 and 6, leading cutting edges 5a and 6a arranged in the direction of rotation and introduction of said screw in order to make said threads self-tapping.

According to a first variant, the bone screw 1 with discontinuous double thread 5, 6 can comprise an internal bore 13 enabling it to be guided in the bone tissues by means of a guide, which is not represented and which is introduced beforehand into said bone tissue.

Figure 4:
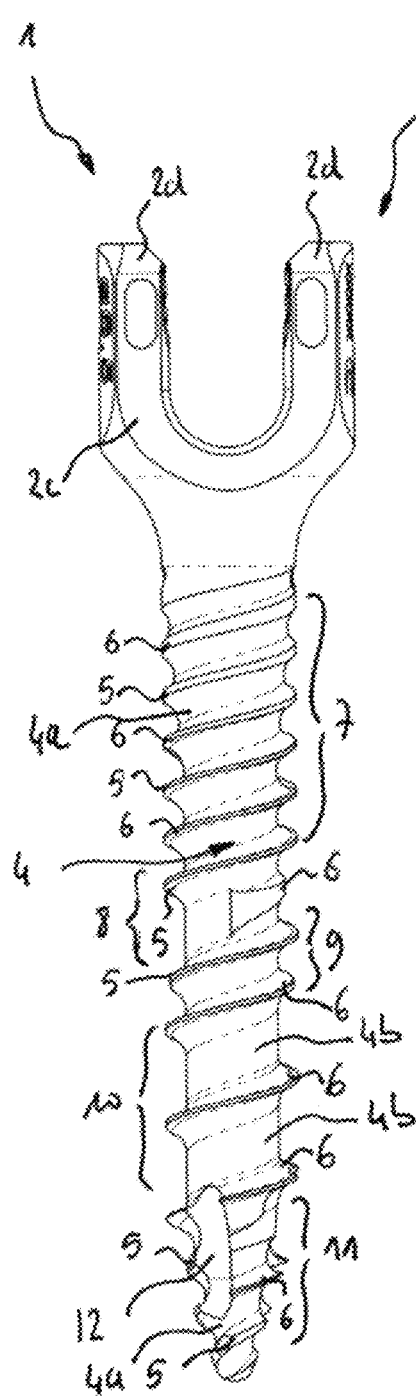
FIGS. 4 and 5 are front and cross-sectional views showing an embodiment variant of the drive head of a discontinuously double-threaded bone screw according to the present invention.
Figure 5:
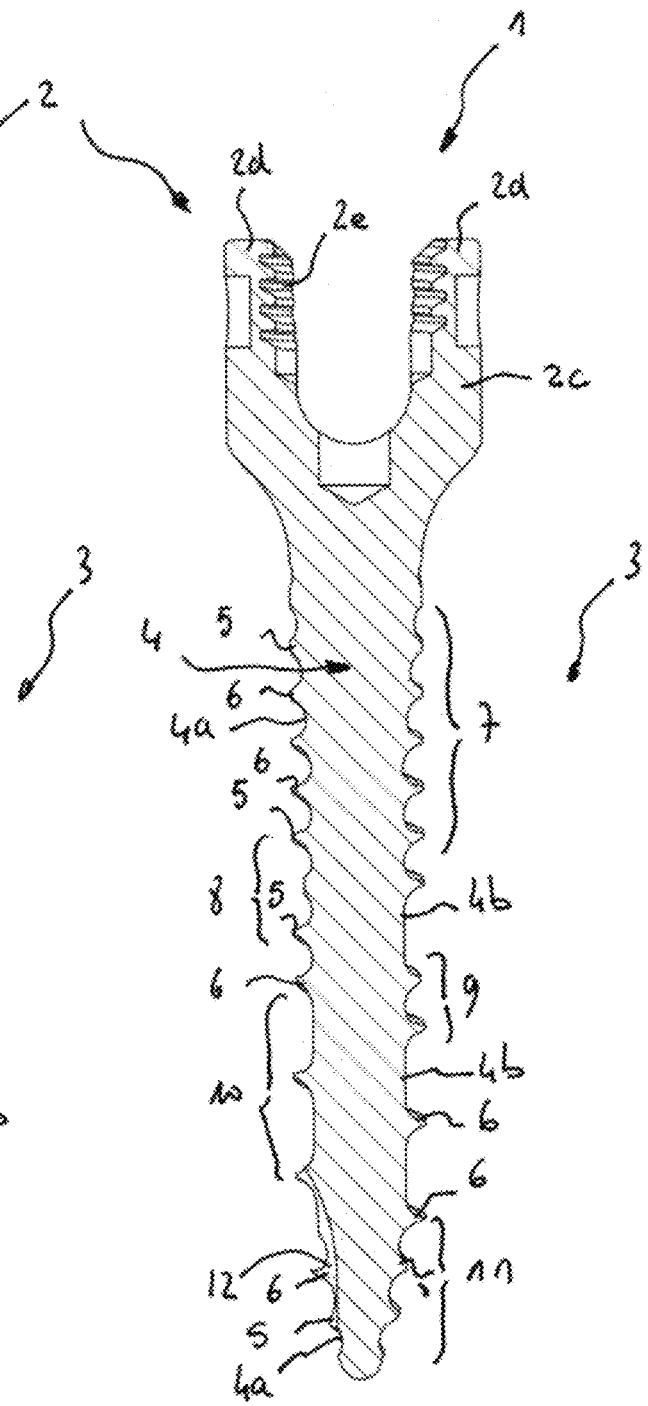

In FIGS. 4 and 5, a bone screw 1 is illustrated, which comprises a drive head 2 extended by an anchoring body 3 consisting of a cylindro-conical core 4 over which extend at least two discontinuous cylindro-conical threads 5, 6 ensuring the anchoring of said screw 1 in the different components of the bone tissue.

In this variant, the drive head 2 consists of a single-piece head 2c having a U-shaped profile firmly attached to the anchoring body 3 having the anchoring portions 7, 8, 9, 10 with different profiles so as to ensure an anchoring corresponding to the different hardnesses and strength of the bone tissue.

The single-piece head 2c having a U-shaped profile of which the internal portion of the vertical branches 2d comprises a threading 2e cooperating with a tightening screw, which is not represented, for the immobilization of, for example, a linking rod of a spinal osteosynthesis device.

Moreover, it should be understood that the above description was given only as an example, and that it in no way limits the scope of the invention, which would not be exceeded by replacing the execution details described by any other equivalent.

The invention claimed is:

1. A discontinuously double-threaded bone screw (1) for attachment of a prosthesis or an implant against a bone portion, comprising:
    a drive head (2); and
    an anchoring body (3) extending from the drive head (2), the anchoring body including a cylindro-conical core (4), over which extends at least two cylindro-conical threads (5, 6) to ensure an anchoring of the bone screw (1) to a bone,
    the anchoring body (3) also including, over an entire length of the anchoring body and starting from a location of the drive head (2), anchoring portions of different profiles to ensure an anchoring of the bone screw corresponding to different hardnesses and strengths of the bone,
    the anchoring portions of the anchoring body (3) including, below the drive head (2),
        a first anchoring portion (7) having a conical core (4a) and two threads (5, 6) with a cylindrical profile of identical pitch,
        a second anchoring portion (8) having a cylindrical core (4b) and a single cylindrical thread (5) over a ¼ turn,
        a third anchoring portion (9) having a cylindrical core (4b) and two threads (5, 6) with a cylindrical profile over a ½ turn,
        a fourth anchoring portion (10) having a cylindrical core (4b) and a single thread (6) with cylindrical profile over n turn as a function of a total length of the bone screw (1), and
        a fifth anchoring portion (11) having a conical core (4a) and two threads (5, 6) with conical profile forming a tip of said bone screw.

2. The discontinuously double-threaded bone screw according to claim 1, wherein the first anchoring portion (7) includes two threads (5, 6) with a cylindrical profile of identical pitch offset on a periphery of the conical core (4a) by 180°.

3. The discontinuously double-threaded bone screw according to claim 1, wherein the fourth anchoring portion (10) includes a cylindrical thread (6) that is different from the cylindrical thread (5) of the second anchoring portion (8).

4. The discontinuously double-threaded bone screw according to claim 1, further comprising:
an internal bore (13).

5. The discontinuously double-threaded bone screw according to claim 1, wherein the drive head (2) has a head with a spherical profile (2a), and an internal portion with a recess (2b) for placement of a tool.

6. The discontinuously double-threaded bone screw according to claim 1, wherein the drive head (2) has a single-piece head (20) with a U-shaped profile configured to receive a tightening screw for immobilization of an osteosynthesis device.

7. The discontinuously double-threaded bone screw according to claim 1, wherein the two threads of the fifth anchoring portion (11) are self-tapping threads.

* * * * *